US006632405B2

(12) United States Patent
Lua

(10) Patent No.: US 6,632,405 B2
(45) Date of Patent: Oct. 14, 2003

(54) SOLAR-POWER BATTERY AIR FRESHENER WITH OSCILLATING FAN

(75) Inventor: Edgardo R. Lua, 245 Banawe St., cor Sgt. Rivera, Quezon City (PH)

(73) Assignee: Edgardo R. Lua, Quezon (PH)

( * ) Notice: Subject to any disclaimer, the term of this patent is extended or adjusted under 35 U.S.C. 154(b) by 0 days.

(21) Appl. No.: 10/185,071

(22) Filed: Jun. 26, 2002

(65) Prior Publication Data

US 2002/0197188 A1 Dec. 26, 2002

Related U.S. Application Data

(60) Provisional application No. 60/302,090, filed on Jun. 26, 2001.

(51) Int. Cl.[7] .................................................. A61L 9/00

(52) U.S. Cl. ....................... 422/124; 422/123; 422/305; 422/306

(58) Field of Search ................................ 422/123, 124, 422/305, 306, 125

(56) References Cited

U.S. PATENT DOCUMENTS 3,990,848 A 11/1976 Corris ......................... 422/49
4,647,428 A 3/1987 Gyulay .......................... 422/4
4,808,347 A 2/1989 Dawn .......................... 261/30
5,342,584 A 8/1994 Fritz et al. .................. 422/124
5,938,076 A * 8/1999 Ganzeboom ................. 222/23

FOREIGN PATENT DOCUMENTS

GB 2119499 A * 11/1983 ............ F24F/7/007
GB 2132280 A * 7/1984 ........... B65D/83/14

* cited by examiner

*Primary Examiner*—Robert J. Warden, Sr.
*Assistant Examiner*—Sean E. Conley

(57) ABSTRACT

A solar-power battery air freshener includes a housing (100) with an oscillating fan (61) for emitting a fragrance to the surrounding environment. A solar-power battery (20) utilizes energy derived from natural sunlight or light emitted from a regular light fixture in order to provide power to an oscillating device wherein a fan (61) is connected. The oscillating device includes a circuit (44), a coil (45), and magnets (46) connected to vertical iron plates (41, 42). A bracket (60) is attached to the iron plate (41) in such a manner that a fan (61) can be attached to the bracket. A fragrance container (81) is located directly below the fan (61). The oscillating movement of the fan (61) disperses the fragrance emitted from the fragrance container (81) out of the housing through air vents (105) and into the room or vehicle being freshened.

1 Claim, 3 Drawing Sheets

SIDEVIEW

Solar-Power Battery Air Freshener
with Oscillating Fan

SIDEVIEW

Solar-Power Battery Air Freshener with Oscillating Fan

PERSPECTIVE VIEW

Solar-Power Battery Air Freshener
with Oscillating Fan

HOUSING

Solar-Power Battery Air Freshener
with Oscillating Fan

SOLAR-POWER BATTERY AIR FRESHENER WITH OSCILLATING FAN

This application claims the benefit of Provisional Application Serial No. 60/302,090 Application Title, Solar-power battery air freshener device with oscillating fan, filed Jun. 26, 2001.

BACKGROUND OF THE INVENTION

1. Field of the Invention

The present invention relates generally to air freshener and more specifically it relates to a solar-power battery air freshener with oscillating fan for providing a device with solar-power battery utilizing the energy derived from natural sunlight or light emitted from regular room light fixture. The solar-power battery is operationaly connected to an oscillating device wherein a fan is connected. The oscillating or to and fro movement of the fan moves fragrance emitted from the volatile substance of the fragrance out of the housing to the room or vehicle being freshened.

2. Description of the Prior Art

It can be appreciated that air freshener have been in use for years. Typically, air freshener are comprised of U.S. Pat. No. 5,342,584, an air freshener device and cartridge with battery as means of power. U.S. Pat. No. 3,711,023, an air freshener device utilizing an air conditioning system which releases the evaporated volatile substance into the air to produce an odor. U.S. Pat. No. 3,990,848, an air flow induction device air freshening apparatus with a fan mounted in the housing. A fan driven by a motor is connected with the battery. U.S. Pat. No. 4,647,428, a room air freshening device that uses light bulb for vaporization of liquid. It works when the light bulb is turned on to heat and vaporize fragrance to permeate the room. U.S. Pat. No. 4,808,347, an air freshening apparatus which is plugged into a standard cigarette lighter socket of vehicles, utilizing an electric motor within the housing with a peopeller fastened to its shaft.

The main problem with conventional air freshener are that, as in U.S. Pat. Nos. 5,342,584 and 3,990,848, the devices need the usage of batteries. The utilization of batteries to power the devices need more attention to the operation of the devices, need the constant change of batteries, add more cost to the device because of the cost of batteries. Another problem with conventional air freshener are that, as in U.S. Pat. No. 3,711,023, the device uses the air conditioning system to release the evaporated volatile substance into the air to produce an odor. The utilization of the air conditioning system makes the device depended on the time the air conditioning system is working. Another problem with conventional air freshener are that, as in U.S. Pat. No. 4,647,428, the room freshener device utilizes a light bulb that is plugged to the electrical system. The light bulb has to be turned on and at the same time consume electricity to function. Another problem with existing products is that, as in U.S. Pat. No. 4,808,347, the air freshening device is plugged into a standard device as in this case the cigarette lighter socket in a vehicle. Another problem with existing products is that, as in U.S. Pat. No. 4,808,347, the air freshening device is plugged into a standard cigarette lighter socket in a vehicle. Again, the device is dependent on another device as in this case the cigarette lighter, which on occasion may not be functioning.

While these devices may be suitable for the particular purpose to which they address, they are not as suitable for providing a device with solar-power battery utilizing the energy derived from natural sunlight or light emitted from regular room light fixture. The solar-power battery is operationaly connected to an oscillating device wherein a fan is connected. The oscillating or to and fro movement of the fan moves fragrance emitted from the volatile substance of the fragrance out of the housing to the room or vehicle being freshened. The main problem with conventional air freshener are that, as in U.S. Pat. Nos. 5,342,584 and 3,990,848, the devices need the usage of batteries. The utilization of batteries to power the devices need more attention to the operation of the devices, need the constant change of batteries, add more cost to the device because of the cost of batteries. Another problem is that, as in U.S. Pat. No. 3,711,023, the device uses the air conditioning system to release the evaporated volatile substance into the air to produce an odor. The utilization of the air conditioning system makes the device depended on the time the air conditioning system is working. Also, another problem is that, as in U.S. Pat. No. 4,647,428, the room freshener device utilizes a light bulb that is plugged to the electrical system. The light bulb has to be turned on and at the same time consume electricity to function. Another problem with existing products is that, as in U.S. Pat. No. 4,808,347, the air freshening device is plugged into a standard device as in this case the cigarette lighter socket in a vehicle. Another problem with existing products is that, as in U.S. Pat. No. 4,808,347, the air freshening device is plugged into a standard cigarette lighter socket in a vehicle. Again, the device is dependent on another device as in this case the cigarette lighter, which on occasion may not be functioning.

In these respects, the solar-power battery air freshener with oscillating fan according to the present invention substantially departs from the conventional concepts and designs of the prior art, and in so doing provides an apparatus primarily developed for the purpose of providing a device with solar-power battery utilizing the energy derived from natural sunlight or light emitted from regular room light fixture. The solar-power battery is operationaly connected to an oscillating device wherein a fan is connected. The oscillating or to and fro movement of the fan moves fragrance emitted from the volatile substance of the fragrance out of the housing to the room or vehicle being freshened.

SUMMARY OF THE INVENTION

In view of the foregoing disadvantages inherent in the known types of air freshener now present in the prior art, the present invention provides a new solar-power battery air freshener with oscillating fan construction wherein the same can be utilized for providing a device with solar-power battery utilizing the energy derived from natural sunlight or light emitted from regular room light fixture. The solar-power battery is operationaly connected to an oscillating device wherein a fan is connected. The oscillating or to and fro movement of the fan moves fragrance emitted from the volatile substance of the fragrance out of the housing to the room or vehicle being freshened.

The general purpose of the present invention, which will be described subsequently in greater detail, is to provide a new solar-power battery air freshener with oscillating fan that has many of the advantages of the air freshener mentioned heretofore and many novel features that result in a new solar-power battery air freshener with oscillating fan which is not anticipated, rendered obvious, suggested, or even implied by any of the prior art air freshener, either alone or in any combination thereof.

To attain this, the present invention generally comprises a solar-power battery 20 is attached to a housing 100 which contains a circuit 44, a coil 45, and magnets 46 connected to a vertical iron plates 41 & 42. The vertical iron plate's 41 & 42 upper portion is connected to a shaft which gives the iron plate 41 & 42 the mobility to oscillate due to the reaction of the coil 45 and the magnet 46. A bracket 60 is attached to the iron plate 41 in such a manner that a fan 61 can be attached to the bracket. The container 81 which has fragrance emitting substance is directly under the fan 61. When the oscillating motion of the fan 61 takes place because of the interaction of all the component parts of my invention, fragrance air is forced out of the housing 100 through the air vents 105 strategically located on the housing 100 of my invention. The solar-power 20 battery is a device which absorbs the energy emitted from sunlight or light from regular light fixtures and transforms the energy into power. The housing 100 is a formed or injected container made of elastic or molded material. A circuit 44 is a path which provides a continuous passage of electricity. A coil 45 is a winded wire usually made of copper. The fan 61 is a molded or injected component structure which is designed to move or circulate air when in operation. The container 81 is a molded, injected, or stamped structure normally used to hold substances in solid or liquid form. The fragrance is the scent emitted by pleasant odor producing substance. The air vent 103 is a passage normally in a structure which permits air flow to and from the structure. The magnet 46 is a body which attracts metal. The iron plate 41 & 42 is a formed metal structure. A shaft is a cylindrical, slender metal object. A bracket 60 is a formed part designed to serve as a support.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a solar-power battery air freshener with oscillating fan that will overcome the shortcomings of the prior art devices.

An object of the present invention is to provide a solar-power battery air freshener with oscillating fan for providing a device with solar-power battery utilizing the energy derived from natural sunlight or light emitted from regular room light fixture. The solar-power battery is operationaly connected to an oscillating device wherein a fan is connected. The oscillating or to and fro movement of the fan moves fragrance emitted from the volatile substance of the fragrance out of the housing to the room or vehicle being freshened.

Another object is to provide a solar-power battery air freshener with oscillating fan that will solve the disadvantages of prior arts wherein they either need to be manually operated, need to utilize batteries, need to be plugged to electrical socket.

Another object is to provide a solar-power battery air freshener with oscillating fan that utilizes natural sunlight or light emitted by regular room light fixtures.

Another object is to provide a solar-power battery air freshener with oscillating fan that it is self contained. It does not need anymore manual operations, does not need anymore batteries, does not need to be plugged into electrical current. All the device needs is ample natural sunlight or light emitted by regular room light fixtures.

Another object is to provide a solar-power battery air freshener with oscillating fan that is economical. There are no added cost incurred for the solar power battery operated air freshener to operate other than the fragrance which in all air freshener is also an additional component of the whole air freshener device.

Another object is to provide a solar-power battery air freshener with oscillating fan that needs minimal maintenance. There are no batteries to change, nothing to manually operate, no need to create electrical system for the invention to plug in. The invention works safely while unattended.

Another object is to provide a solar-power battery air freshener with oscillating fan that utilizes a swinging apparatus using the solar battery as power source. The solar battery, with the energy it absorbs from sunlight or light from regular light fixture, supplies in the form of short discharge current or electric energy to the driving coils. The permanent magnet has a repulsive or attractive magnetic pole arrangement. When an electric current is fed to said driving coil from the circuit, said permanent magnet being relatively movable with respect to the driving coil is capable of performing a swinging motion.

Another object is to provide a solar-power battery air freshener with oscillating fan that is usable in any rooms or vehicles where ample sunlight or light emitted from regular room light fixture.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
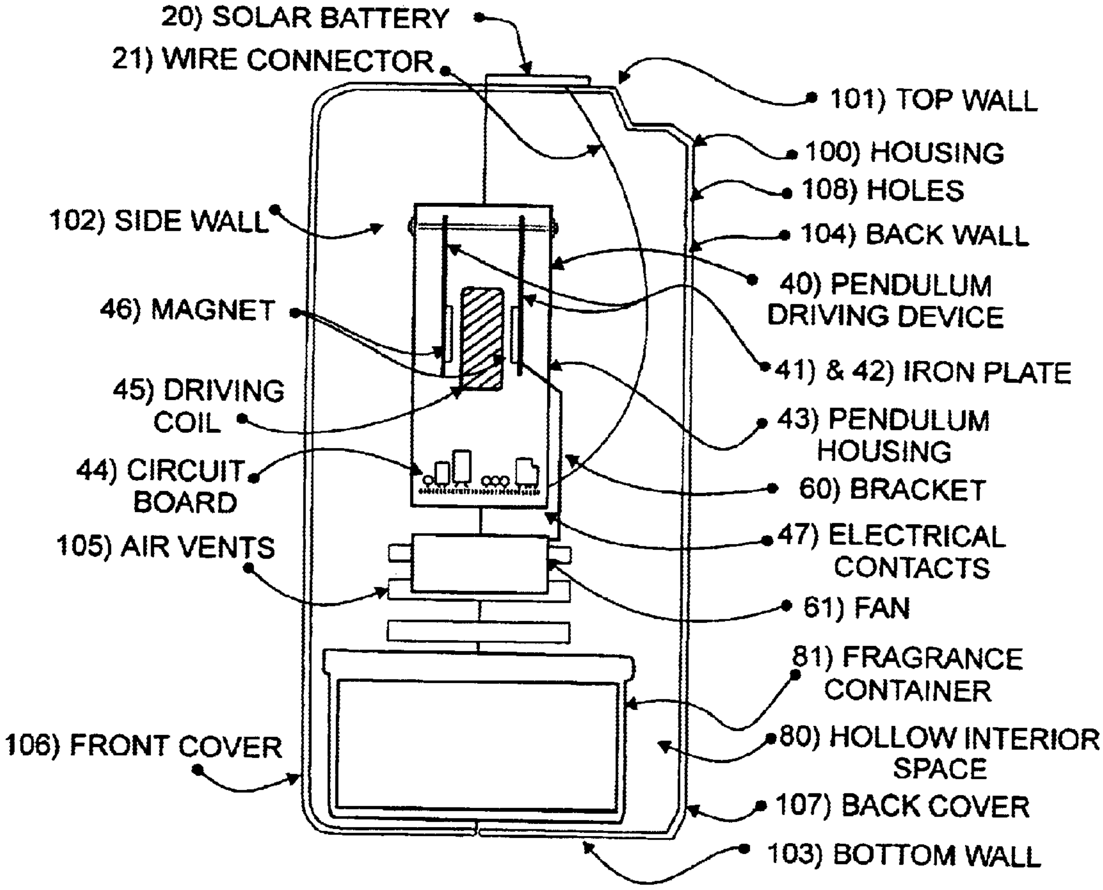
FIG. 1 is a perspective view of the invention.

Turning now descriptively to the drawings, in which similar reference characters denote similar elements throughout the several views, the attached figures illustrate a solar-power battery air freshener with oscillating fan, which comprises a solar-power battery 20 is attached to a housing 100 which contains a circuit 44, a coil 45, and magnets 46 connected to a vertical iron plates 41 & 42. The vertical iron plate's 41 & 42 upper portion is connected to a shaft which gives the iron plate 41 & 42 the mobility to oscillate due to the reaction of the coil 45 and the magnet 46. A bracket 60 is attached to the iron plate 41 in such a manner that a fan 61 can be attached to the bracket. The container 81 which has fragrance emitting substance is directly under the fan 61. When the oscillating motion of the fan 61 takes place because of the interaction of all the component parts of my invention, fragrance air is forced out of the housing 100 through the air vents 105 strategically located on the housing 100 of my invention. The solar-power 20 battery is a device which absorbs the energy emitted from sunlight or light from regular light fixtures and transforms the energy into power. The housing 100 is a formed or injected container made of elastic or molded material. A circuit 44 is a path which provides a continuous passage of electricity. A coil 45 is a winded wire usually made of copper. The fan 61 is a molded or injected component structure which is designed to move or circulate air when in operation. The container 81 is a molded, injected, or stamped structure normally used to hold substances in solid or liquid form. The fragrance is the scent emitted by pleasant odor producing substance. The air vent 105 is a passage normally in a structure which permits air flow to and from the structure. The magnet 46 is a body which attracts metal. The iron plate 41 & 42 is a formed metal structure. A shaft is a cylindrical, slender metal object. A bracket 60 is a formed part designed to serve as a support.

The solar-power 20 battery is a device which absorbs the energy emitted from sunlight or light from regular light fixtures and transforms the energy into power. As shown in FIGS. through 1 to 2, the solar-power battery is a structure that utilizes no chemical reaction to produce electrical power and it has no moving parts. Its main function is to absorb sunlight or light from light fixtures to be converted into electrical energy. Solar batteries can be arranged into large groupings which may be composed of many thousand of individual cells. Because there no moving parts, they do not require service or fuels. The basic structure and principles of a solar battery can be described as light enters the device through a layer of material called the antireflection layer which absorbs and traps the light falling on the solar cell and transmits this light into the energy layers of the solar cell which usually is made of silicon oxides or titanium dioxide. The conversion of light into electrical energy called photovoltaic effect occurs in the three energy-conversion layers namely the top junction layer, absorber layer, and the back junction layer. The solar battery also has two additional layers called the electrical contact layers. The layers allow electric current to flow in and out of the cell where light enters. There is the back electrical layer which functions as an electrical contact and conductor. When light falls on the cell, free electrons occur as a result of the interaction of the light with the absorber layer where the energy of an electron increases from a ground state energy to an excited energy state. This results in and energetic, free electrons. The electrons are collected by the electrical contact layers for use in external circuit where they can do useful work. Also known as semiconductors. The semiconductors can absorb light to the thickness of one-hundredth of a centimeter or less. When the electron is lifted to its excited state by consuming light energy, it moves to the external circuit to the electric field and it is in this external circuit that the electron will dissipate its excess energy in some devices as a motor. When the energy is expended when the solar battery produces electric current to the motor, the above mentioned process starts all over again. The solar-power battery may be arranged into groupings which may be composed of thousands of cells and can function as power stations. Solar battery convert sunlight into electrical energy that can be used in industrial, commercial, and residential applications. As in consumer products such as electronic toys, hand held calculators as in this invention, to power an oscillating as an air freshener.

Figure 2:
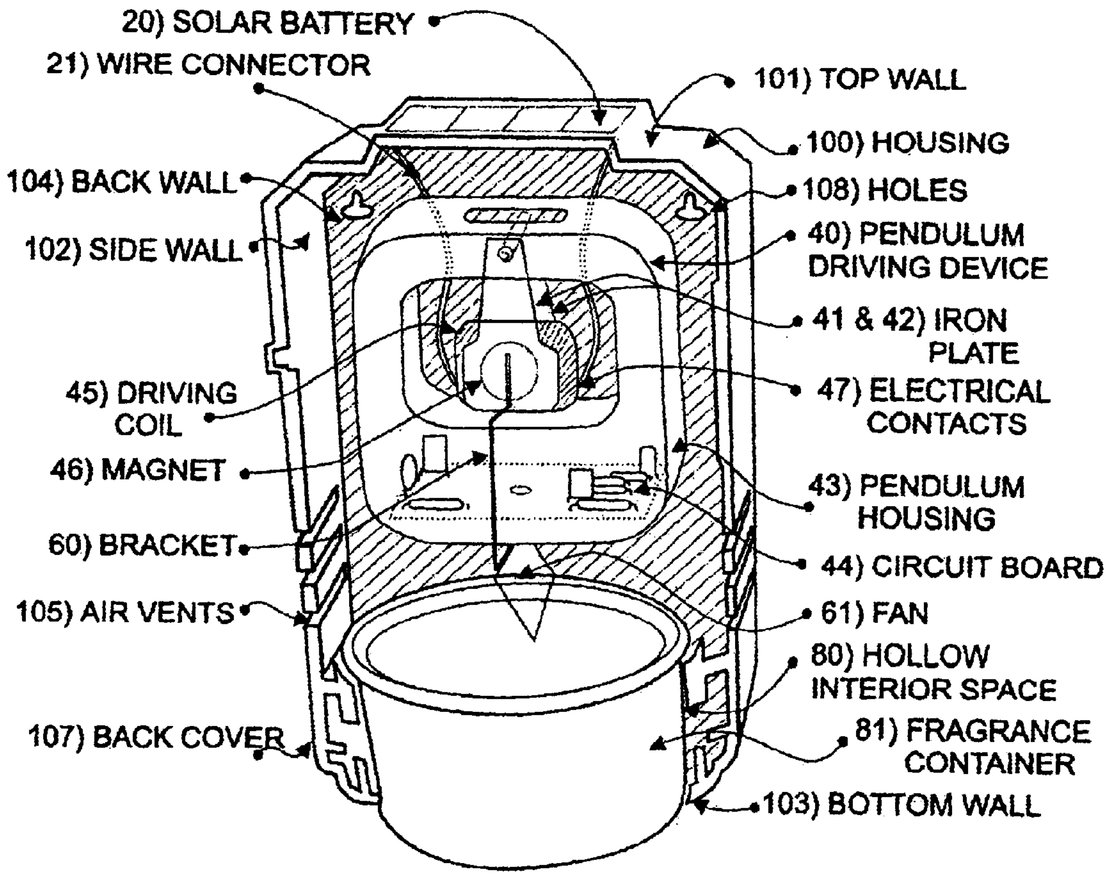
FIG. 2 is a side view of the invention.
Figure 3:
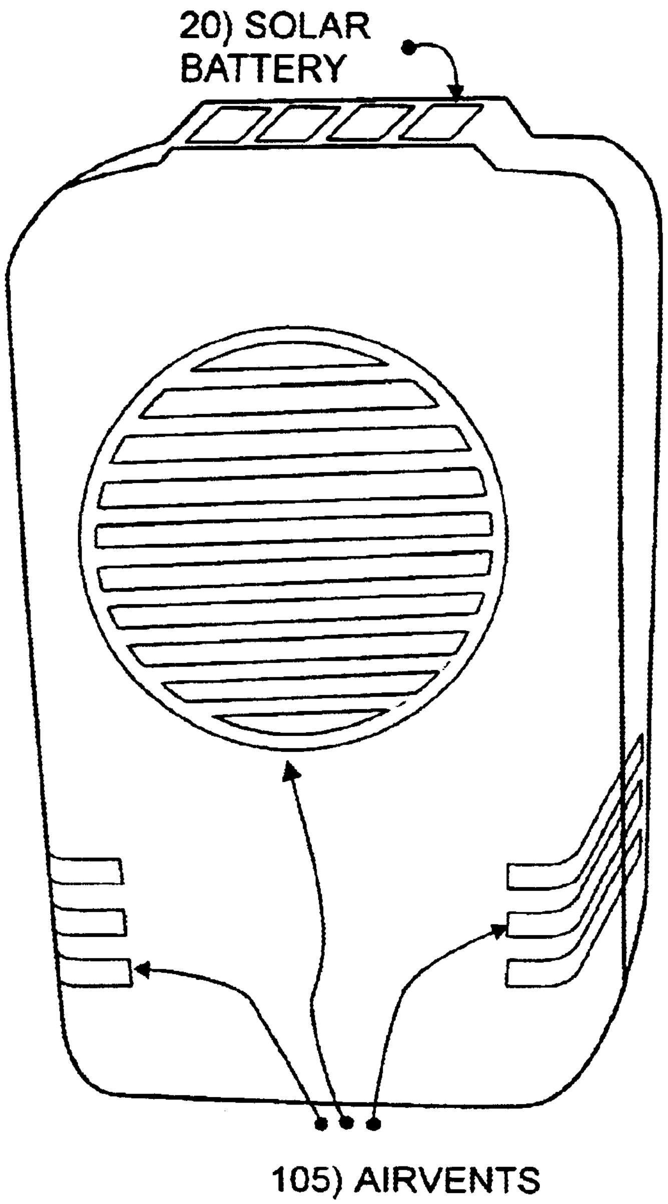
FIG. 3 is a perspective view of the air freshener dispenser cover.

The housing 100 is a formed or injected container made of elastic or molded material. The housing as shown in FIGS. 1 to 3, is a molded, injected, or stamped container made of materials that can be shaped into various forms to hold other objects, parts or component of a product, device or apparatus. The housing may also be constructed from various substances and shaped into numerous forms to contain or hold many kinds of objects, devices, or apparatus into one whole component part which can be adhered to or connected to other components or object.

A circuit 44 is a path which provides a continuous passage of electricity. The circuit is a path which provides continuous passage of electricity. It usually contains a driving coil, transistor capacitor. When an electric current is fed to said driving coil from the power source, a magnetic field is generated which reacts repulsively or attractively to magnetic pole arrangements of a magnet. A circuit is composed of a network of transistors, transformers, capacitors, connecting wires and other electronic components within a single device.

A coil 45 is a winded wire usually made of copper. The coil is circular or cylindrical shaped object made of current-carrying wire designed to produce a magnetic field. or desinged to provide a resistance or inductance in a circuit. Coils are usually relative to functions of electrical in nature. It is composed of winded current-carrying wire designed to produce magnetic field normally by placing a soft iron core within to produce an electromagnetic field when activated. Coils are usually relative to functions of electrical in nature. It is composed of winded current-carrying wire designed to to produce magnetic field normally by placing a soft iron core within to produce an electromagnetic field when activated.

The fan 61 is a molded or injected component structure which is designed to move or circulate air when in operation. Fan is a device for stirring air. It can come in different sizes and shapes and can drive air movement with a to and fro, oscillating movement depending on the design of the device. It can be made of various materials to include paper, fabric, plastic, metal to name a few and can be manufactured through injection, moulding, and stamping. There are quite a few designs to a fan. It can be straight, bent, formed into a propeller design and many others shapes and dimensions. The main feature of which is that the device can stir or move air usually connected to another device that aids its oscillating motion or circular or rotary motion.

The container 81 is a molded, injected, or stamped structure normally used to hold substances in solid or liquid form. Container is any device or apparatus that will hold another device, object or substance. The conatiner comes in a multitude of shapes and configuration and design and can be constructed with various injectable, mouldable and stampable materials such as paper, plastic, in plates, metal or glass. It's main objective is to hold other materials or substances.

The fragrance is the scent emitted by pleasant odor producing substance. Fragrance is also called scent. Usually referred to as an odor that is pleasant to smell. It is often contained in mixture of water, and other volatile substances which is emitted in the air to freshen specific areas. Fragrance can come in the forms of sprays, candles, gel, water or petroleum based essences.

The air vent 103 is a passage normally in a structure which permits air flow to and from the structure. Air vent is a passage or an outlet where in air can readily flow in and out of a container or housing. An air vent which is a passage or an outlet can be designed in so many different ways, for as long as that it would provide an avenue where air can move in and out from its containment. It can be situated in any part of the container or housing.

The magnet 46 is a body which attracts metal. A magnet is a body that attracts iron or steel. A magnet has a positive and negative polarity. It is with this feature that it reacts with other objects to cause attractive or draw against another object having another positive and negative polarity.

The iron plate 41 & 42 is a formed metal structure. The iron plate is a formed metal part. The iron plate is a formed metal that could be used to attach other materials. It is sturdy enough to be welded, glued, to other objects.

A shaft is a cylindrical, slender metal object. A shaft is a cylindrical, slender object normally made of metal. Shafts are normally used to aid in motion or mobility. As in the invention the shaft allows the iron plate to swing.

A bracket 60 is a formed part designed to serve as a support. Bracket is an attachment or a support to another object. Brackets can be made of sturdy material, it is commonly referred to as something that would lend to support another object or matter.

The interconnection of my invention starts with the solar-power battery being attached to the housing of the device. The solar-power battery has a negative and positive polarity wherein electrical wires are connected. The wires are in turn connected inside the housing to the circuit which is firmly set in place in the interior of the housing utilizing the housing design to snugly fit the circuit board. With the interaction of the component parts of the invention. An oscillating movement of the fan agitates the air right on top of the container where fragrance vapor from the fragrance in the container. The container has the fragrance medium and is strategically positioned close to the fan so that the volatile vapor of the fragrance will easily move towards the air vents of the housing to the room or vehicle. The solar-power battery can be attached to the housing. It can be positioned in such a manner that it will be able to absorb the light or energy source. This position can be on the top or on the sides or the bottom of the housing directly or indirectly facing the light or energy source, or the sunlight or light from regular room light fixture. The solar-power battery is connected with electric wires to the circuit board, which is in turn connected to the coil. As the coil is energized, the magnetic field created between the coil and the magnets makes the iron plate where the magnets are attached to move in a pendulum manner. The bracket is also attached to the iron plate. Said brackets hold a light weight fan positioned directly over the container which contains the fragrance. Due to the interaction of the magnet from the oscillation of the iron plate, the fan which is connected to the bracket moves as well in the same pendulum manner. It activates the air right on the top surface of the container where vapor fragrance which has been emitted from the fragrance in the container is present. Said fragranced air is forced out of the housing through the air vents, thus freshening the room or vehicle.

Referring now to FIGS. 1 through 3 and particularly to FIG. 1, a solar-power driven air freshener according to the present invention is shown. The air freshener has a rectangular box shaped housing 100, which has a side wall 102, a top wall 101, bottom wall 103 and back wall 104 preferable made of durable, electrically non-conductive material such as polypropylene. Preferably the housing 100 is fabricated by injection molding. As may be seen best by referring to FIG. 1, the interior space of the rectangular box shaped housing 100 contains a pendulum driving device 40. Within the driving device 40 an electric circuit board 44. The electric circuit board 44 fits exactly within the hollow interior space 80 of the compartment within the housing 100. As shown in FIG. 1, the solar battery wire connectors 21 are connected to the electrical contacts 47 and of the circuit board 44 which is snugly fit inside the pendulum housing 43. As shown in FIGS. 1 and 2 the hollow interior space 80 of the rectangular box shaped housing accomodates a fan 61 attached to the bracket 60. The bracket 60 is connected to the iron plate 41 & 42. Said iron plates 41 & 42 when activated create an oscillating like motion. As may be seen best by referring to FIG. 1 and 2 air vents 105 are strategically provided on the housing 100 to permit free movement of air moved by the circular rotation of the fan 61. When an electric current is fed to the driving coil 45 through its oscillating circuit on the printed circuit board 44 for a short time in a stationary state of the bracket 60, a magnetic field is created on the driving coil 45 opposed thereto through a slight gap. With this electromagnetic force, the position of the magnet 46 at the lower end of the pendulum shifts from the neutral point in the direction such that the initial slight eccentrcity is enlarged of the swing motion and the bracket starts its inertial swing motion while retrieving under a gravitational resting force. As the bracket 60 swings, the fan 61 blade also begins to swing. The swinging motion of the fan 61 blade creates a stream of air to scatter the scent of the fragrance container 81 to the room or vechicle through the air vents 105. As may be seen best by referring to FIG. 1, the back wall 104 of the housing 100 has a front cover 106 that fits snugly to the back cover 107 of the hollow housing 100 wherein air vent 105 can also be located. to allow air passage to and from the housing 100. As shown in FIGS. 1 and 2, the air freshener includes a container 81 whose dimension fit snugly into the lower hollow section of the housing 100. The container 81 which is made of a material that could hold fragrance substance that would blend into a fragrance medium set in place within the container 81. The back cover 107 of the housing 100 and the front section cover 106 of the housing 100 fits perfectly which provide a convenient means for taking off the front cover 106 of the air freshener without tools and for replacing container 81 after its scent has dissipated. Also described previously, the novel design of the solar-power battery air freshener according to the present invention allows easy removal and replacement of container 81 without requiring tools. As illustrated in the back wall 104 of the of the back housing 100, holes 108 are made to optionally combined with the air freshener which provides a convinient means of securing the housing 100 of the air freshener on the wall of the rooms inside a building with screws. Likewise, double sided adhesive tape is also adhered to the back outer side of the housing 100 to provide another adhesive means of the solar-power air freshener on walls or surfaces of rooms or vehicles.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A solar-power air freshener device comprising a front cover and a back cover, said front cover including a front wall, a top wall, a pair of opposing side walls, and a bottom wall, said back cover including a back wall, a top wall, a pair of opposing side walls, and a bottom wall, wherein the front cover and back cover are attached to form a housing, said bottom wall having a hole provided therein, said side walls and said front cover having air vents permitting air flow, a fragrance container containing scented materials inserted and held on said bottom wall through said hole, a solar battery mounted on said top wall, and a pendulum driving device secured on said back wall, said pendulum driving device including a driving coil, wherein the energy from the solar battery energizes the pendulum driving coil, said driving coil being held between pivotally attached metal plates on a pendulum housing, each of the metal plates having a magnet attached thereon, and one of the metal plates having a pendulum extending downwardly thereon and a fan blade attached on said pendulum.

* * * * *